United States Patent [19]

Schriewer et al.

[11] Patent Number: 4,816,451
[45] Date of Patent: Mar. 28, 1989

[54] ANTIBACTERIAL 1,8-BRIDGED 4-QUINOLONECARBOXYLIC ACIDS

[75] Inventors: Michael Schriewer; Klaus Grohe, both of Odenthal; Hermann Hagemann, Leverkusen; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 68,074

[22] Filed: Jun. 29, 1987

[30] Foreign Application Priority Data

Jul. 15, 1986 [DE] Fed. Rep. of Germany ....... 3623757

[51] Int. Cl.$^4$ ................. A61K 31/555; A61K 31/535; A61K 31/55; C07D 498/06
[52] U.S. Cl. ................................. 514/185; 514/211; 514/230.2; 540/541; 540/544; 544/101
[58] Field of Search ................. 540/541, 544; 544/101; 514/185, 211, 230, 233, 234, 236, 230.2

[56] References Cited

U.S. PATENT DOCUMENTS

4,382,892  5/1983  Hayakawa et al. ............. 544/101 X

FOREIGN PATENT DOCUMENTS

0047005  3/1982  European Pat. Off.
0206076  12/1986  European Pat. Off.

OTHER PUBLICATIONS

Patent Abstracts of Japan, vol. 9, No. 160 (C-289) [1883] Jul. 4, 1985.
Patent Abstracts of Japan, vol. 7, No. 151 (C-174) [1296] Jul. 2, 1983.
Patent Abstracts of Japan, vol. 7, No. 167 (C-177) [1312] Jul. 22, 1983.
Patent Abstracts of Japan, vol. 7, No. 53 (C-154) [1198] Mar. 3, 1983.
Patent Abstracts of Japan, vol. 10, No. 31 (C-327) [2088] Feb. 6, 1986.
Patent Abstracts of Japan, vol. 10, No. 63 (C-332) [2120] Mar. 13, 1986.

*Primary Examiner*—Richard L. Raymond
*Attorney, Agent, or Firm*—Sprung Horn Kramer & Woods

[57] ABSTRACT

Antibacterially effective 1,8-bridged 4-quinolone-3-carboxylic acids and derivatives of the formula

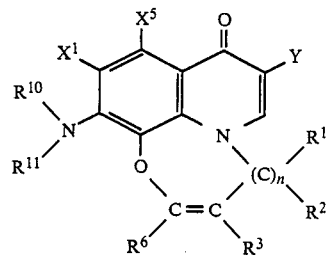

in which
Y represents a carboxyl group, a nitrile group, an ester group —COOR$^7$ or an acid amide group —CONR$^8$R$^9$,
X$^1$ represents hydrogen, nitro, alkyl with 1-3 carbon atoms, or halogen,
X$^5$ represents hydrogen, halogen or alkyl,
R$^{10}$ and R$^{11}$ complete an optionally substituted ring, and
n is 0 or 1, and pharmaceutically usable hydrates, salts and esters thereof.

12 Claims, No Drawings

ANTIBACTERIAL 1,8-BRIDGED 4-QUINOLONECARBOXYLIC ACIDS

The invention relates to new 1,8-bridged 4-quinolone-3-carboxylic acids, processes for their preparation and their use as medicaments, in particular as antibacterial agents in human and veterinary medicine.

The invention provides 1,8-bridged 4-quinolone-3-carboxylic acids and derivatives of the formula I

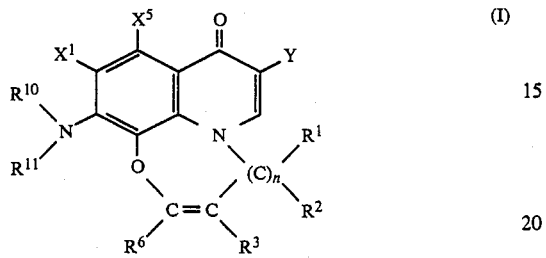

in which

Y represents a carboxyl group, a nitrile group, an ester group —COOR$^7$ or an acid amide group —CONR$^8$R$^9$, wherein R$^7$ represents alkyl, preferably C$_1$–C$_4$-alkyl, and R$^8$ and R$^9$ independently of one another represent hydrogen or alkyl, preferably C$_1$–C$_4$-alkyl, and R$^9$ can also be optionally substituted phenyl, X$^1$ represents hydrogen, nitro, alkyl, preferably with 1–3 carbon atoms, or halogen, preferably fluorine, X$^5$ can be hydrogen, halogen, preferably Cl or F, or alkyl, preferably with 1–3 C atoms, in particular methyl, R$^{10}$ and R$^{11}$, together with the nitrogen atom to which they are bonded, form a 5- or 6-membered heterocyclic ring which can additionally contain the atoms or groups —O—, —S—, —SO—, —SO$_2$—,

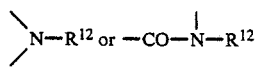

as a ring member and which can optionally be mono-, di- or trisubstituted on the carbon atoms by identical or different substituents from the group comprising C$_1$–C$_4$-alkyl, phenyl or cyclohexyl which are optionally mono-, di- or trisubstituted by chlorine, fluorine, bromine, methyl, phenyl, hydroxyl, methoxy, benzyloxy, nitro or piperidino, 2-thienyl, hydroxyl, alkoxy with 1 to 3 carbon atoms, amino, methylamino, ethylamino, aminomethyl, methylaminomethyl and ethylaminomethyl, wherein R$^{12}$ represents hydrogen, a branched or unbranched alkyl, alkenyl or alkinyl group with 1 to 6 carbon atoms, which can optionally be substituted by one or two hydroxyl groups of alkoxy, alkylamino or dialkylamino groups with in each case 1 to 3 carbon atoms for an alkyl radical, the cyano group, the alkoxycarbonyl group with 1 to 4 carbon atoms in the alcohol part, a phenylalkyl group which has up to 4 carbon atoms in the aliphatic part and is optionally substituted in the phenyl radical, a phenacyl radical which is optionally mono- or disubstituted by hydroxyl, methoxy, chlorine or fluorine, or an oxoalkyl radical with up to 6 carbon atoms, or furthermore denotes a radical COR$^{13}$ or SO$_2$R$^{14}$, wherein R$^{13}$ represents hydrogen, straight-chain or branched alkyl which has 1 to 4 carbon atoms and is optionally substituted by 1 or 2 substituents from the series comprising amino, alkoxycarbonyl with 1 to 3 carbon atoms in the alkyl part, carboxyl, alkoxy with 1 to 3 carbon atoms and halogen, such as chlorine, bromine and fluorine, alkoxy with 1 to 4 carbon atoms, amino or alkylamino or dialkylamino with 1 to 5 carbon atoms in the alkyl part and R$^{14}$ represents straight-chain or branched alkyl with 1 to 3 carbon atoms, and R$^1$, R$^2$, R$^3$ and R$^6$ represent hydrogen, an alkyl group, preferably with 1–6 carbon atoms, which is optionally mono- or polysubstituted by halogen, in particular chlorine or fluorine, or furthermore nitro, cyano, hydroxyl, or alkoxy or alkylmercapto with 1–3 carbon atoms in the alkyl part, or an optionally by halogen, nitro, alkyl, or alkoxy or alkylmercapto, preferably with in each case up to 3 carbon atoms, hydroxyl, aryloxy, arylthio, aryl in each case preferably representing phenyl or naphthyl, cyano or an ester radical, preferably with 1-3 carbon atoms in the alcohol part substituted phenyl radical, naphthyl radical or preferably 5- or 6-membered heterocyclic radical with preferably N and/or O as hetero-atoms, such as, for example, the thiophene, furan, pyrrole, thiazole, pyridine or pyrimidine radical, and n denotes 0 or 1, and their pharmaceutically usable hydrates or salts, preferably alkali metal, alkaline earth metal, silver and guanidinium salts, and their esters.

The compounds have a high antibacterial activity. They are therefore suitable as active compounds for human and veterinary medicine. They can also be used as intermediate products for the preparation of other bactericides.

Preferred compounds of the formula (I) are those in which

Y represents a carboxyl group, a nitrile group or an ester group —COOR$^7$, wherein R$^7$ is methyl or ethyl, X$^1$ represents fluorine, X$^5$ represents hydrogen and R$^{10}$ and R$^{11}$, together with the nitrogen atom to which they are bonded, can form a 5- or 6-membered heterocyclic ring which can additionally contain an oxygen atom or the groups N—R$^{12}$ or —CO—N—R$^{12}$ as a ring member and which can optionally be mono- or disubstituted on the carbon atoms by C$_1$–C$_2$-alkyl, cyclohexyl, phenyl which is optionally substituted by chlorine, fluorine, methyl, phenyl, hydroxyl, methoxy, benzyloxy, nitro or piperidino, 2-thienyl or hydroxyl, wherein R$^{12}$ represents hydrogen, a branched or unbranched alkyl group with 1 to 3 carbon atoms, which can optionally be substituted by one or two hydroxyl groups, or a phenacyl radical, an oxoalkyl radical with up to 4 carbon atoms or a radical $COR^{13}$,
wherein
$R^{13}$ denotes hydrogen or alkyl with one or two carbon atoms, and
in which
n, $R^1$, $R^2$, $R^3$ and $R^6$ have the abovementioned definitions.

The compounds of the formula (I) according to the invention are obtained by a process in which quinolonecarboxylic acid derivatives of the formula (II)

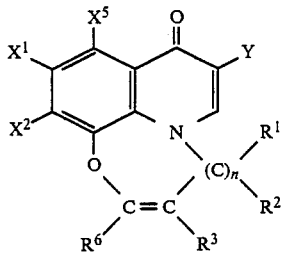
(II)

in which
the radicals $X^1$, $X^5$, $R^1$, $R^2$, $R^3$ and $R^6$, Y and n have the abovementioned meanings and $X^2$ represents halogen, preferably chlorine or fluorine,
are reacted with amines of the formula (III)

(III)

in which
$R^{10}$ and $R^{11}$ have the abovementioned meanings, if appropriate in the presence of acid-binding agents.
(Method A).

This process does not necessarily have to be carried out such that $R^{10}$ and $R^{11}$ in the amines of the formula (III) already have their final meaning which they have in the compounds of the formula I according to the invention. Rather, it is also possible to use precursors to the radicals $R^{10}$ and $R^{11}$ in a first step, these then being converted into the final form of $R^{10}$ and $R^{11}$ in one or more secondary reaction steps.

Thus, for example, compounds of the formula (I) according to the invention can be obtained by a process in which a 10-(1-(piperazinyl)compound (for n=0) or 11-(1-piperazinyl) compound (for n=1) of the formula (IV)

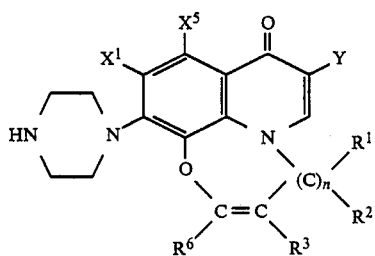
(IV)

in which
$X^1$, $X^5$, $R^1$, $R^2$, $R^3$ and $R^6$, Y and n have the abovementioned meanings, and the piperazinyl radical on the carbon atoms can be substituted in the manner described for $R^{10}$ and $R^{11}$, for example by 1, 2 or 3 radicals from the group comprising $C_1$–$C_4$-alkyl, 2-thienyl and optionally substituted cyclohexyl and phenyl,
are reacted with compounds of the formula (V)

$$R^{12}X \quad (V)$$

in which
$R^{12}$ has the abovementioned meaning, but cannot be hydrogen, and
X denotes fluorine, chlorine, bromine, iodine, hydroxyl, acyloxy, ethoxy, phenoxy or 4-nitrophenoxy,
if appropriate in the presence of acid-binding agents.
(Method B).

In this reaction procedure, the piperazinyl radical in the 10- or 11-position can thus be introduced in a first reaction step by the method first mentioned-which leads to the compounds (IV) which are already according to the invention—and other substituents desired, in this case $R^{12}$ for example, can then be introduced in a secondary step.

In another embodiment of the process according to the invention, compounds of the formula (I) according to the invention are obtained by a procedure in which 10-(1-piperazinyl)quinolonecarboxylic acid derivatives (n=0) or 11-(1-piperazinyl)quinolonecarboxylic acid derivatives (n=1) of the formula (IV) in which the piperazinyl radical can be substituted on the carbon atoms in the manner already mentioned, for example by 1, 2 or 3 radicals from the group comprising $C_1$–$C_4$-alkyl, 2-thienyl and optionally substituted cyclohexyl and phenyl, are reacted with Michael acceptors of the formula (VI)

$$B-CH=CH_2 \quad (VI)$$

in which
B represents CN, CO—$R^{15}$ or $COOR^{16}$,
wherein
$R^{15}$ represents methyl or ethyl and
$R^{16}$ represents methyl, ethyl or n- or i-propyl.
(Method C).

If, for example, 1-methylpiperazine and 9,10-difluoro-7-oxo-2-phenyl-7H-pyrido[1,2,3-de][1,4]benzoxazine-6-carboxylic acid are used as starting substances in the reaction by the method mentioned first, the course of the reaction can be represented by the following equation:

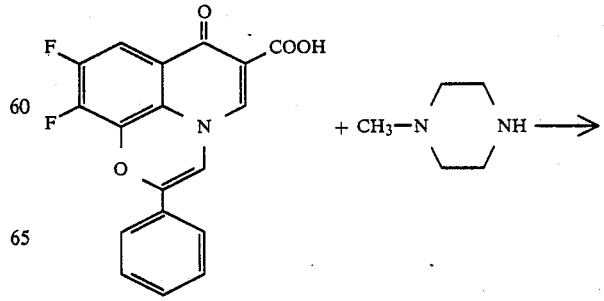

-continued

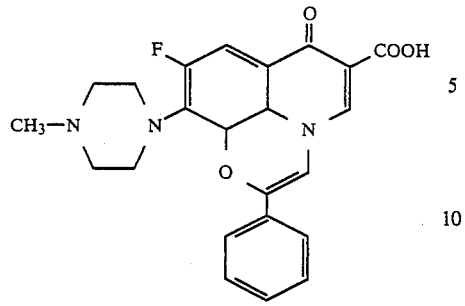

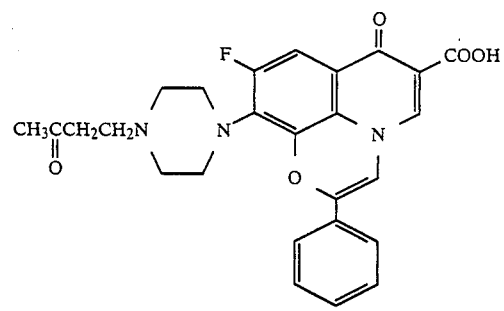

If, for example, ethyl iodide and 9-fluoro-7-oxo-2-phenyl-10(1-piperazinyl)-7H-pyrido[1,2,3-de][1,4]benzoxazine-carboxylic acid are used as starting substances in the reaction by the modified method, the course of the reaction can be represented by the following equation:

The quinolonecarboxylic acids of the formula (II) which can be used as starting substances in the process according to the invention can be prepared in accordance with the following equation (process 1).

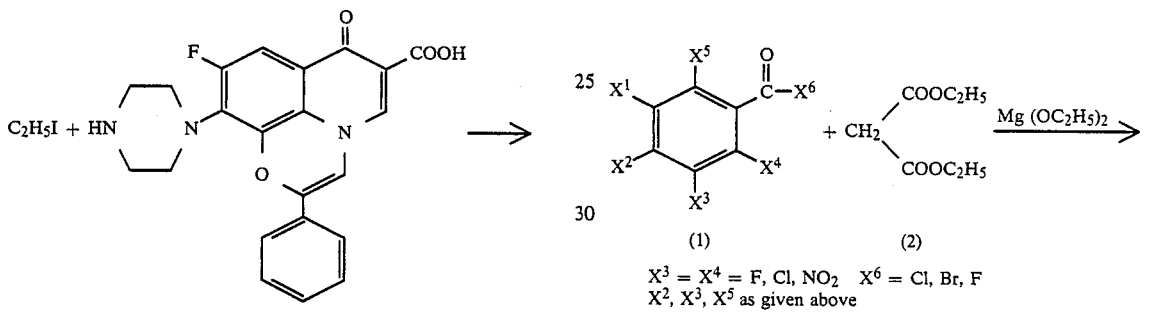

$X^3 = X^4 = F, Cl, NO_2$   $X^6 = Cl, Br, F$
$X^2, X^3, X^5$ as given above

The reaction with Michael acceptors with, for example, 9-fluoro-7-oxo-2-phenyl-10(1-piperazinyl)-7H-pyrido[1,2,3][1,4]benzoxazine-6-carboxylic acid and methyl vinyl ketone as starting substances can be represented by the following equation:

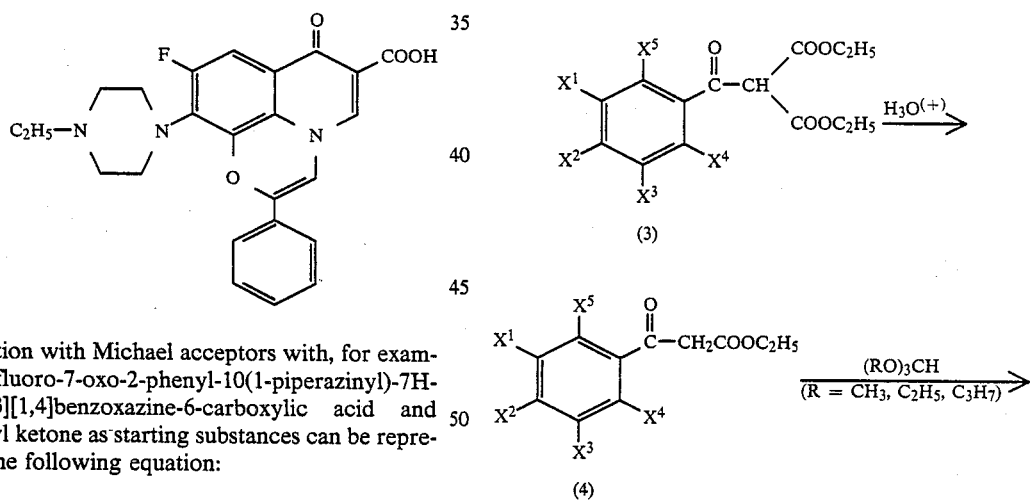

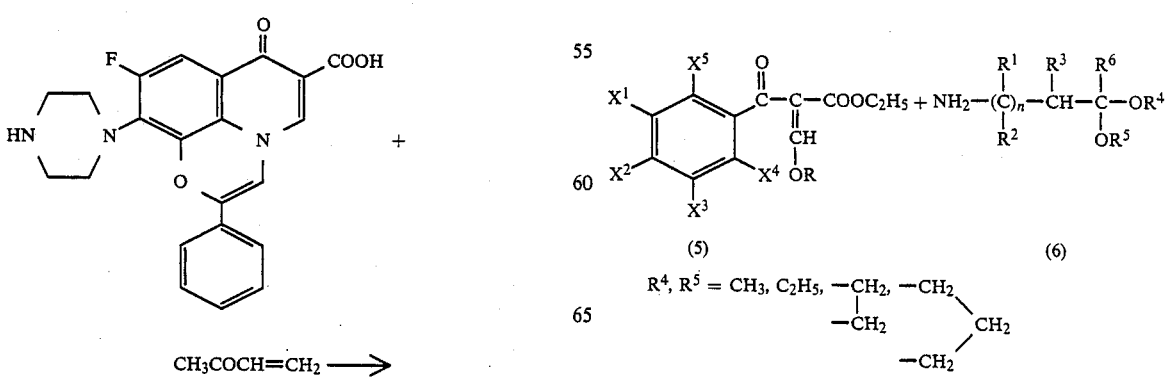

$R^4, R^5 = CH_3, C_2H_5, -CH_2, -CH_2$
                              $|$         $\backslash$
                          $-CH_2$      $CH_2$
                                          $/$
                              $-CH_2$ -continued

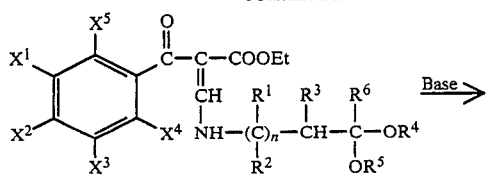

(7)

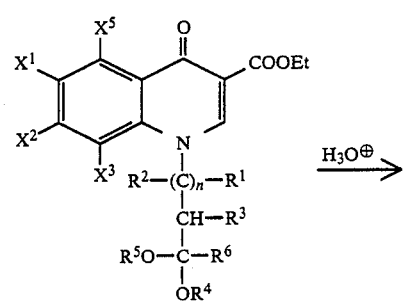

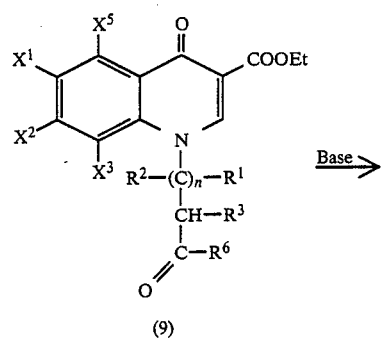

(9)

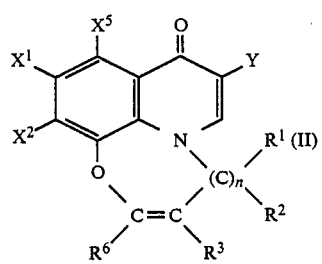

According to this reaction, diethyl malonate (2) is acylated with the corresponding benzoyl fluoride or chloride (1) in the presence of magnesium ethylate to give the benzoyl malonate (3) (Organicum, 3rd edition 1964, page 438).

Partial hydrolysis and decarboxylation of (3) in an aqueous medium with catalytic amounts of sulphuric acid or p-toluenesulphonic acid gives a good yield of the ethyl benzoylacetate (4), which is converted with triethyl orthoformate/acetic anhydride into the ethyl 3-ethoxyacrylate (5). The reaction of (5) with the corresponding amine (6) in a solvent, such as, for example, methylene chloride, alcohol, chloroform, cyclohexane or toluene, leads to the desired intermediate product (7) in a slightly exothermic reaction.

The cyclization reactions (7)→(8) are carried out in a temperature range of about 60° to 300° C., preferably 80° to 180° C.

Diluents which can be used are dioxane, dimethyl sulphoxide, N-methylpyrrolidone, sulpholane, hexamethylphosphoric acid triamide and, preferably, N,N-dimethylformamide.

Possible acid-binding agents for this reaction stage are potassium tert.-butanolate, butyl-lithium, lithium-phenyl, phenylmagnesium bromide, sodium methylate, sodium hydride, sodium carbonate or potassium carbonate, and particularly preferably potassium fluoride or sodium fluoride.

The hydrolysis of the acetal or ketal (8) to form (9) is carried out in acid solution, preferably in aqueous mineral acid solution.

The cyclization of (9)→(11) which takes place in the last step is carried out in a temperature range from about 60° to 300°, preferably 80° to 180° C.

Diluents which can be used are alcohol, dioxane, dimethylsulphoxide, hexamethylphosphoric acid triamide and, preferably, water.

Possible acid-binding agents for this reaction stage are potassium tert.-butanolate, butyllithium, phenyllithium, phenylmagnesium bromide, sodium methylate, sodium hyride and, preferably, potassium hydroxide or sodium hydroxide.

The 2,3,4,5-tetrafluorobenzoyl chloride used as starting substances for this synthesis route (process 1) are known.

3,5-Dichloro-2,4-difluoro-benzoyl fluoride (boiling point 97°/29 mbar; $n_d^{20}=1.5148$) and 5-chloro-2,3,4-trifluorobenzoyl fluoride (boiling point 66°–70°/20 mbar; $n_D^{20}=1.4764$) are obtained side by side by heating tetrachlorobenzoyl chloride to elevated temperatures with potassium fluoride in sulpholane:

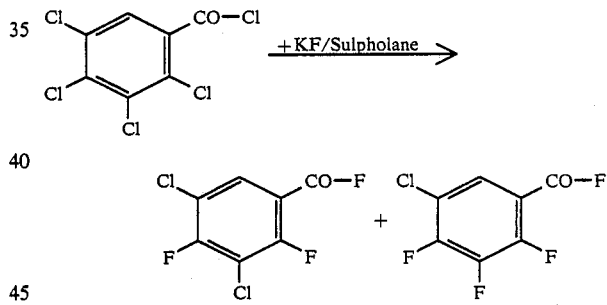

The chlorination of 2,4,5-trifluorobenzoic acid in chlorosulphonic acid leads to 3-chloro-2,4,5-trifluorobenzoic acid, which is reacted as the crude product with thionyl chloride to give 3-chloro-2,4,5-trifluorobenzoyl chloride (boiling point 94°/18 mbar; $n_D^{20}=1.5164$):

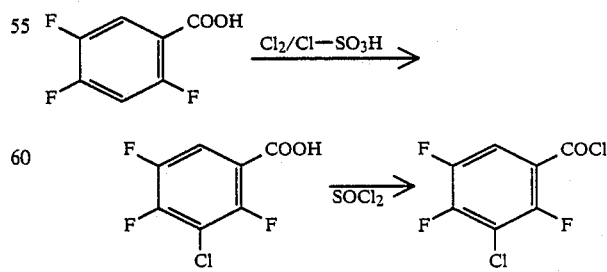

2,4-Dichloro-5-fluoro-3-nitro-benzoyl chloride is obtained by nitration of 2,4-dichloro-5-fluoro-benzoic acid, which is known, to give 2,4-dichloro-5-fluoro-3- nitro-benzoic acid and reaction thereof with thionyl chloride.

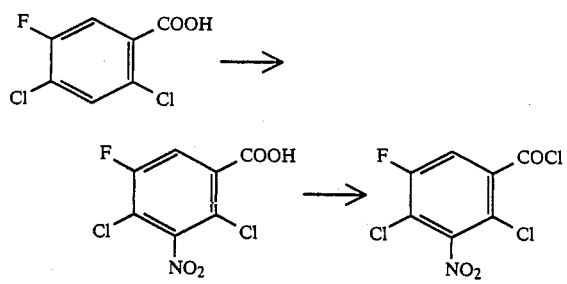

The amines of the formula (6) used as starting substances are known. Examples which may be mentioned are: aminoacetaldehyde dimethyl acetal, aminoacetaldehyde diethyl acetal, 2-amino-propionaldehyde dimethyl acetal, 2-aminocyclohexanone dimethyl ketal, 2-aminomethyl-1,3-dioxane, 2-aminomethyl-1,3-dioxane and 2-(1-amino-1-ethyl)-1,3-dioxane.

In the case where n=0, the quinolonecarboxylic acids of the formula II which can be used as starting substances by method A can likewise be obtained in accordance with the following equation (process 2).

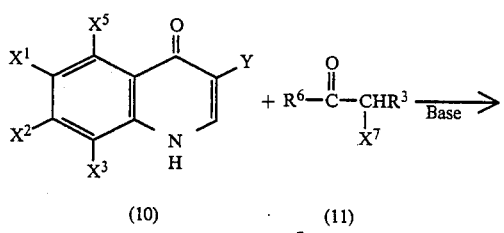

(10)　　　　　(11)
　　　　　$X^7$ = Cl, Br

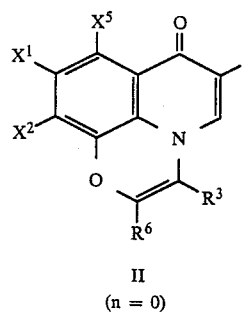

II
(n = 0)

A 4-quinolone-3-carboxylic acid derivative (10) in which $X^1$, $X^2$, $X^3$ and Y have the abovementioned meaning is accordingly reacted with an α-halogenocarbonyl compound 11 in which $R^3$ and $R^6$ have the abovementioned meaning in the presence of a base, the alkylation and cyclization to 11 being carried out in one step in a so-called one-pot reaction.

The reaction is carried out in a temperature range from 60° to 300° C., preferably 80° to 180° C.

Diluents which can be used are dioxane, dimethyl sulphoxide, N-methylpyrrolidone, sulpholane, hexamethylphosphoric acid triamide and, preferably, N,N-dimethylformamide.

Possible acid-binding agents for this reaction stage are potassium tert.-butanolate, butyllithium, phenyllithium, phenylmagnesium bromide, sodium methylate, sodium hydride and, preferably, sodium carbonate and potassium carbonate.

The 4-quinolone-3-carboxylic acid derivatives and 4-hydroxy-3-quinolinecarboxylic acid derivatives of the formula (10) used as starting substances for this synthesis route (process 2) are known. Examples which may be mentioned are: ethyl 7-chloro-6,8-difluoro-4-hydroxy-5-nitro-3-quinolinecarboxylate and ethyl 6,7,8-trifluoro-4-hydroxy-3-quinolinecarboxylate.

The α-halogenocarbonyl compounds used as starting substances are known. As an example there may be mentioned: chloroacetaldehyde, chloroacetone, ω-bromoacetophenone, 2-chlorocyclohexanone, 2-chlorobutanone and 1,3-dichloroacetone.

Example of a tablet according to the invention

Each tablet contains:

| | |
|---|---|
| Compound of Example 1 | 583.0 mg |
| Microcrystalline cellulose | 55.0 mg |
| corn starch | 72.0 mg |
| Insoluble poly-(1-vinyl-2-pyrrolidone) | 30.0 mg |
| Highly disperse silicon dioxide | 5.0 mg |
| Magnesium stearate | 5.0 mg |
| | 750.0 mg |

The lacquer shell contains:

| | |
|---|---|
| Poly-(O—hydroxypropyl-O—methyl)-cellulose 15 cp | 6.0 mg |
| Macrogol 4000, recommended International Polyethylene glycols (DAB) | 2.0 mg |
| Titanium-(IV) oxide | 2.0 mg |
| | 10.0 mg |

The compounds according to the invention exhibit, coupled with a low toxicity, a broad antibacterial spectrum against Gram-positive and Gram-negative germs, in particular against Enterobacteriaceae; above all against those which are resistant towards various antibiotics, such as, for example, penicillins, cephalosporins, aminoglycosides, sulphonamides and tetracyclines.

These useful properties enable them to be used as chemotherapeutic active compounds in medicine and as substances for the preservation of inorganic and organic materials, in particular all types of organic materials, for example polymers, lubricants, paint, fibers, leather, paper and wood, and foodstuffs and water.

The compounds according to the invention are active against a very broad spectrum of microorganisms. With their aid, it is possible for Gram-negative and Gram-positive bacteria and bacteria-like microorganisms to be combated and for the diseases caused by these pathogens to be prevented, alleviated and/or cured.

The compounds according to the invention are particularly active against bacteria and bacteria-like microorganisms. They are therefore particularly suitable in human and animal medicine for the prophylaxis and chemotherapy of local and systemic infections caused by these pathogens.

For example, local and/or systemic diseases caused by the following pathogens or by mixtures of the following pathogens can be treated and/or prevented: Gram-positive cocci, for exxample staphylococci (*Staph. aureus* and *Staph. epidermidis*) and streptococci (*Strept. agalactiae, Stretp. faecalis, Strept. pneumoniae* and *Strept. pyogenes*); Gram-negative cocci (*Neisseria gonorrhoeae*) and Gram-negative rod-shaped bacillae, such as Enterobacteriaceae, for example *Escherichia* coli, Haemophilus influenzae, Citrobacter (*Citrob. freundii* and *Citrob. divernis*), Salmonella and Shigella; and furthermore Klebsiellae (*Klebs. pneumoniae* and *Klebs. oxytoca*), Enterobacter (*Ent. aerogenes* and *Ent. agglomerans*), Hafnia, Serratia (*Serr. marcescens*), Proteus (*Pr. mirabilis, Pr. rettgeri* and *Pr. vulgaris*), Providencia and Yersinia, and the genus Acinetobacter. The antibacterial spectrum moreover includes the genus Pseudomonas (*Ps. aeruginosa* and *Ps. maltophilia*) as well as strictly anaerobic bacteria, such as, for example, *Bacteroides fragilis*, representatives of the genus Peptococcus, Peptostreptococcus and the genus Clostridium; and furthermore mycoplasmas (*M. pneumoniae, M. hominis* and *M. urealyticum*) and mycobacteria, for example *Mycobacterium tuberculosis*.

The above list of pathogens is merely by way of example and is in no way to be interpreted as limiting. Examples which may be mentioned of diseases which are caused by the pathogens or mixed infections mentioned and can be prevented, alleviated or cured by the compounds according to the invention are:

Infectious diseases in humans, such as, for example, otitis, pharyngitis, pneumonia, peritonitis, pyelonephritis, cystitis, endocarditis, systemic infections, bronchitis (acute and chronic), septic infections, diseases of the upper respiratory tract, diffuse panbronchiolitis, pulmonary emphysema, dysentery, enteritis, liver abscesses, urethritis, prostatitis, epididymitis, gastrointestinal infections, bone and joint infections, cystic fibrosis, skin infections, postoperative wound infections, abscesses, phlegmons, wound infections, infected burns, burn wounds, infections in the oral region, infections following dental operations, osteomyelitis, septic arthritis, cholecystitis, peritonitis with appendicitis, cholangitis, intraabdominal abscesses, pancreatitis, sinusitis, mastoiditis, mastitis, tonsillitis, typhus, meningitis and infections of the nervous system, salpingitis, endometritis, genital infections, pelveoperitonitis and eye infections.

As well as in humans, bacterial infections can also be treated in other species. Examples which may be mentioned are: pigs: coli diarrhoea, enterotoxaemia, sepsis, dysentery, salmonellosis, metritis-mastitis-agalactiae syndrome and mastitis; ruminants (cattle, sheep, goats): diarrhoea, sepsis, bronchopneumonia, salmonellosis, pasteurellosis, mycoplasmosis and genital infections; horses: bronchopneumonia, joint ill, puerperal and post-puerperal infections and salmonellosis; dogs and cats: bronchopneumonia, diarrhoea, dermatitis, otitis, urinary tract infections and prostatitis; and poultry (chicken, turkeys, quail, pigeons, ornamental birds and others): mycoplasmosis, *E. coli* infections, chronic respiratory tract diseases, salmonellosis, pasteurellosis and psittacosis.

Bacterial diseases in the rearing and keeping of stock and ornamental fish can likewise be treated, the antibacterial spectrum being extended beyond the abovementioned pathogens to further pathogens, such as, for example, Pasteurella, Brucella, Campylobacter, Listeria, Erysiphelothrix, Coryne bacteria, Borellia, Treponema, Nocardia, Rikettsia and Yersinia.

The present invention includes pharmaceutical formulations which, in addition to non-toxic inert pharmaceutically suitable excipients, contain one or more compounds according to the invention or consist of one or more active compounds according to the invention, and to processes for the preparation of these formulations.

The present invention also includes pharmaceutical formulations in dosage units. This means that the formulation is in the form of individual parts, for example tablets, dragees, capsules, pills, suppositories and ampoules, the active compound content of which correspond to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration, and which usually corresponds to a whole, one half, one third or one quarter of a daily dose.

Non-toxic inert pharmaceutically suitable excipients are to be understood as solid, semi-solid or liquid diluents, fillers and formulation auxiliaries of all kinds.

Preferred pharmaceutical formulations which may be mentioned are tablets, dragees, capsules, pills, granules, suppositories, solutions, suspensions and emulsions, pastes, ointments, gels, creams, lotions, powders and sprays.

Tablets, dragees, capsules, pills and granules can contain the active compound or compounds in addition to the customary excipients, such as (a) fillers and extenders, for example starches, lactose, sucrose, glucose, mannitol and silicic acid, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate, magnesium stearate and solid polyethylene glycols, or mixtures of the substances listed under (a) to (i).

The tablets, dragees, capsules, pills and granules can be provided with the customary coatings and shells, optionally containing opacifying agents, and can also be of a composition such that they release the active compound or compounds only or preferentially in a particular part of the intestinal tract, if required, with delay, examples of embedding compositions which can be used being polymeric substances and waxes.

The active compound or compounds, if appropriate with one or more of the abovementioned excipients, can also be in microencapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starch, tragacanth, cellulose derivatives, polyethylene glycols, silicones, bentonites, silicic acid, talc and zinc oxide, or mixtures of these substances.

Powders and sprays can contain, in addition to the active compound or compounds, the customary excipients, for example lactose, talc, silicic acid, aluminum hydroxide, calcium silicate and polyamide powder, or mixtures of these substances. Sprays can additionally contain the customary propellants, for example chlorofluorohydrocarbons.

Solutions and emulsions can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerol formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol and sorbitan esters, microcrystalline cellulose, aluminum metahydroxide, bentonite, agar-agar and tragacanth, or mixtures of these substances.

The formulation forms mentioned can also contain colouring agents, preservatives and additives of improved smell and taste, for example peppermint oil and eucalyptus oil, and sweeteners, for example saccharin.

The therapeutically active compounds should preferably be present in the abovementioned pharmaceutical formulations in a concentration of about 0.1 to 99.5, preferably about 0.5 to 95% by weight of the total mixture.

The pharmaceutical formulations listed above can also contain other pharmaceutical active compounds, in addition to the compounds according to the invention.

The abovementioned pharmaceutical formulations are prepared in the customary manner by known methods, for example by mixing the active compound or compounds with the excipient or excipients.

The formulations mentioned can be used on humans and animals either orally, rectally, parenterally (intravenously, intramuscularly or subcutaneously), intracisternally, intravaginally, intraperitoneally and locally (powders, ointments or drops), and for the therapy of infections in hollow cavities and body cavities. Possible suitable formulations are injection solutions, solutions and suspensions for oral therapy, and gels, infusion formulations, emulsions, ointments or drops. Ophthalmological and dermatological formulations, silver salts and other salts, ear drops, eye ointments, powders or solutions can be used for local therapy. In the case of animals, intake can also be via the feed or drinking water, in suitable formulations. It is furthermore possible to use gels, powders, dusts, sustained release tablets, premixes, concentrates, granules, pellets, tablets, boli, capsules, aerosols, sprays and inhalates on humans and animals. The compounds according to the invention can also be incorporated into other carrier materials, such as, for example, plastics, (chains of plastic for local therapy), collagen or bone cement.

In general, it has proved advantageous both in human and in veterinary medicine to administer the active compound or compounds according to the invention in total amounts of about 0.5 to about 500, preferably 5 to 100 mg/kg of body weight every 24 hours, if appropriate in the form of several individual doses, to achieve the desired results. An individual dose preferably contains the active compound or compounds according to the invention in amounts of about 1 to about 80, in particular 3 to 30 mg/kg of body weight. However, it may be necessary to deviate from the dosages mentioned, and in particular to do so as a function of the species and body weight of the subject to be treated, the nature and severity of the disease, the nature of the formulation and of the administration of the medicament and the period or interval within which administration takes place.

It can thus in some cases be sufficient to manage with less than the abovementioned amount of active compound, whilst in other cases the abovementioned amount of active compound must be exceeded. The particular optimum dosage and mode of administration required for the active compounds can easily be specified by any expert on the basis of his expert knowledge.

The new compounds can be administered in the customary concentrations and formulations together with the feed or with feed formulations or with the drinking water. Infection by Gram-negative or Gram-positive bacteria can thereby be prevented, alleviated and/or cured and a promotion in growth and an improvement in feed utilization can thereby be achieved.

In general, it has proved advantageous both in human and in veterinary medicine to administer the active compound or compounds according to the invention in total amounts of about 0.5 to about 500, preferably 5 to 100 mg/kg of body weight every 24 hours, if appropriate in the form of several individual doses, to achieve the desired results. An individual dose preferably contains the active compound or compounds according to the invention in amounts of about 1 to about 80, in particular 3 to 30 mg/kg of body weight. However, it may be necessary to deviate from the dosages mentioned, and in particular to do so as a function of the species and body weight of the subject to be treated, the nature and severity of the disease, the nature of the formulation and of the administration of the medicament and the period or interval within which administration takes place.

It can thus in some cases be sufficient to manage with less than the abovementioned amount of active compound, while in other cases the abovementioned amount of active compound must be exceeded. The particular optimum dosage and mode of administration required for the active compounds can easily be specified by any expert on the basis of his expert knowledge.

The new compounds can be administered in the customary concentrations and formulations together with the feed or with feed formulations or with the drinking water. Infection by Gram-negative or Gram-positive bacteria can thereby be prevented, alleviated and/or cured and a promotion in growth and an improvement in feed utilization can thereby be achieved.

The following examples illustrate the invention.

EXAMPLE 1

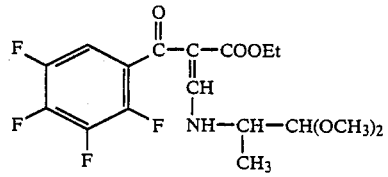

6.4 g of ethyl 3-ethoxy-2-(2,3,4,5-tetrafluorobenzoyl)-acrylate are taken in 8 ml of ethanol. A solution of 2.6 g of 2-amino-propionaldehyde dimethyl acetal in 15 ml of ethanol is added dropwise, while cooling with ice. The mixture is allowed to come to room temperature and is stirred for two hours and then concentrated in vacuo. Yield 8 g of ethyl 2-(2,3,4,5-tetrafluorobenzoyl)-3-(1-methyl-2,2-dimethoxy-1-methyl-ethylamino)-acrylate (crude product, oil).

EXAMPLE 2

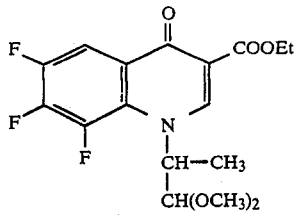

64 g of the crude product from Example 1 and 24 g of K₂CO₃ are heated at 140° C. in 370 ml of dimethylformamide for four hours. The mixture is then poured onto ice. The precipitate is taken up in CH₂Cl₂. The organic phase is washed and dried over Na₂SO₄. Concentration in vacuo gives 50 g of a greasy solid which is purified by washing with ether. Yield 42 g of ethyl 6,7,8-trifluoro-1,4-dihydro-1-(2,2-dimethoxy-1-methyl-ethyl)-4-oxo-3-quinolinecarboxylate.

Melting point: 125°-6° C.

EXAMPLE 3

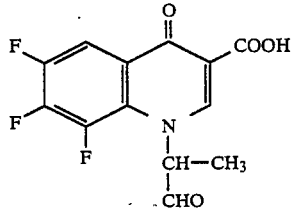

4.4 g of the product from Example 2 are heated at 140° C. together with 15 ml of acetic acid, 13 ml of water and 1.3 ml of sulphuric acid for four hours. After the mixture has been cooled to room temperature, water is added and the solid which has precipitated is isolated. It is sufficiently pure for further reactions. Yield 3.0 g of 6,7,8-trifluoro-1,4-dihydro-4-oxo-1-(1-oxo-2-propyl)-3-quinolinecarboxylic acid.

Melting point 188°-90° C. (decomposition).

EXAMPLE 4

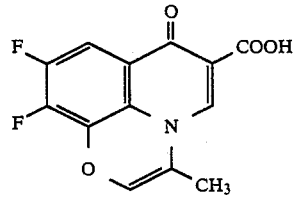

2.2 g of the product from Example 3 are boiled with 0.6 g of NaOH in a mixture of 20 ml of water and 20 ml of ethanol for four hours. After cooling to room temperature the mixture is acidified with dilute hydrochloric acid and the solid formed is isolated.

Yield 1.8 g of 9,10-difluoro-3-methyl-7-oxo-7H pyrido-[1,2,3 de]-[1,4]benzoxazine-6-carboxylic acid.

Melting point 248°-50° C. (decomposition).

EXAMPLE 5

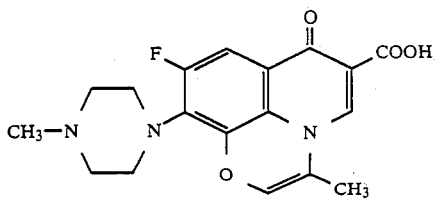

1.6 g of the product from Example 4 and 2.9 g of N-methyl-piperazine are heated at 140° C. in 20 ml of dimethyl sulphoxide for 2.5 hours. After cooling, the mixture is concentrated under a high vacuum. Water is added to the residue. The precipitate is isolated and dried in vacuo at 50° C.

Yield 0.4 g of 9-fluoro-3-methyl-10-(4-methyl-1-piperazinyl)-7-oxo-7H pyrido[1,2,3 de][1,4]benzoxazine-6-carboxylic acid.

Melting point 262°-3° C.

EXAMPLE 6

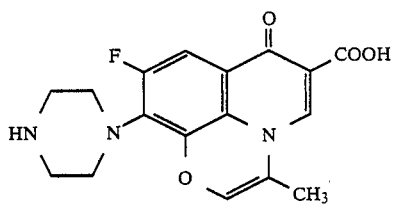

9-Fluoro-3-methyl-10(1-piperazinyl)-7-oxo-7H pyrido[1,2,3 de][1,4]benzoxazine-6-carboxylic acid is obtained analogously to Example 5.

Melting point 270°-2° C. (decomposition).

EXAMPLE 7

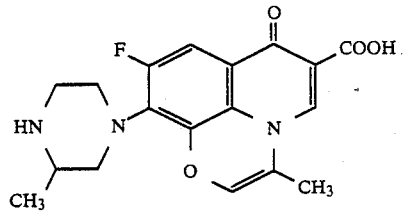

9-Fluoro-3-methyl-10-(3-methyl-1-piperazinyl)-7-oxo-7H pyrido[1,2,3 de][1,4]benzoxazine-6-carboxylic acid is obtained analogously to Example 5.

Melting point 190°-4° C. (decomposition).

EXAMPLE 8

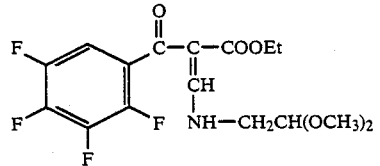

Ethyl 2-(2,3,4,5-tetrafluorobenzoyl)-3-(2,2-dimethoxy-ethylamino)acrylate (oil) is obtained analogously to Example 1 by reaction of ethyl 3-ethoxy-2-(2,3,4,5- tetrafluorobenzoyl)-acrylate with aminoacetaldehyde dimethyl acetal.

EXAMPLE 9

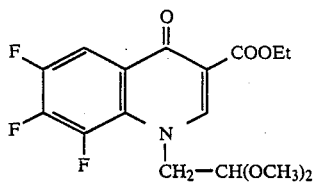

Cyclization of the product from Example 8 analogously to Example 2 gives ethyl 6,7,8-trifluoro-1,4-dihydro-1-(2,2-dimethoxyethyl)-4-oxo-3-quinolinecarboxylate.
Melting point 104°–6° C.

EXAMPLE 10

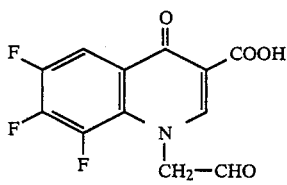

Hydrolysis of the product from Example 9 analogously to Example 3 gives 6,7,8-trifluoro-1,4-dihydro-1-(2-oxo-1-ethyl)-3-quinolinecarboxylic acid.
Melting point 220°–2° C.

EXAMPLE 11

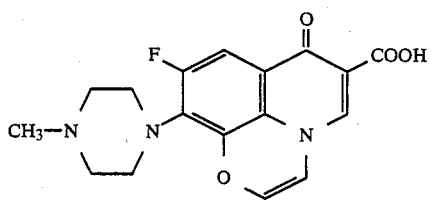

2.85 g of the product from Example 10 and 5.0 g of N-methylpiperazine are heated at 140° C. in 30 ml of dimethylsulphoxide for 2.5 hours. All the volatile constituents are then removed under a high vacuum. The residue is stirred with acetonitrile. The solid is isolated and dried. Yield 2.6 g of 9-fluoro-10-(4-methyl-1-piperazinyl)-7-oxo-7Hpyrido[1,2,3 de][1,4]benzoxazine-6-carboxylic acid.
Melting point >300° C.

EXAMPLE 12

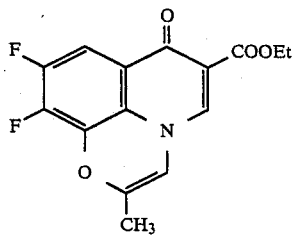

5 g of ethyl 6,7,8-trifluoro-4-hydroxy-3-quinolinecarboxylate, 3.5 g of chloroacetone and 6.6 g of $K_2CO_3$ are heated at 90° C. in 40 ml of dimethylformamide for ten hours. After cooling, all the volatile constituents are stripped off in vacuo. The residue is stirred with water. The solid which remains is isolated, dried and recrystalized from dimethylformamide. Yield 3.4 g of ethyl 9,10-difluoro-2-methyl-7-oxo-7H pyrido[1,2,3 de][1,4]benzoxazine-6-carboxylate.
Melting point 229°–30° C.

EXAMPLE 13

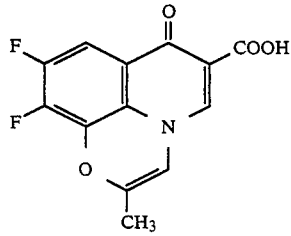

2.6 g of the product from Example 12 are heated at 140° C. together with 10 ml of acetic acid, 8 ml of water and 0.9 ml of $H_2SO_4$ for four hours. After cooling, the mixture is diluted with water. The precipitate is isolated and dried. Yield 2.4 g of 9,10-difluoro-2-methyl-7-oxo-7H pyrido[1,2,3 de][1,4]benzoxazine-6-carboxylic acid.
Melting point >300° C.

EXAMPLE 14

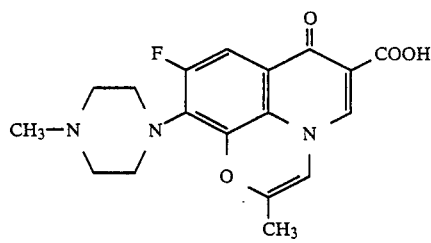

2.4 g of the product from Example 13 and 4.3 g of N-methylpiperazine are heated at 140° C. in 25 ml of dimethylsulphoxide for 2.5 hours. All the volatile constituents are then stripped off in vacuo. The residue is stirred with water. The solid which remains is isolated and dried.
Yield 1.3 g of 9-fluoro-2-methyl-10(4-methyl-1-piperazinyl)-7-oxo-7H pyrido[1,2,3 de][1,4]benzoxazine-6-carboxylic acid.
Melting point 225°–6° C. (decomposition).

EXAMPLE 15

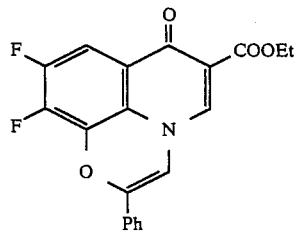

5 g of ethyl 6,7,8-trifluoro-4-hydroxy-3-quinolinecarboxylate, 5.9 g of ω-chloroacetophenone and 6.6 g of $K_2CO_3$ are heated at 90° C. in 40 ml of dimethylformamide for 10 hours. The mixture is then concentrated in vacuo. The residue is stirred with water and the solid is isolated and recrystallized from dimethylformamide.

Yield 2.4 g of ethyl 9,10-difluoro-7-oxo-2-phenyl-7H pyrido[1,2,3 de][1,4]benzoxazine-6-carboxylate.

Melting point 251°–52° C.

EXAMPLE 16

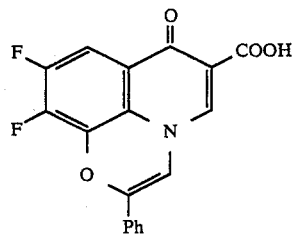

1.9 g of the product from Example 15, 6 ml of acetic acid, 4 ml of water and 0.5 ml of sulphuric acid are boiled for 4 hours. The mixture is then diluted with water and the solid is separated off.

Yield 1.7 g of 9,10-difluoro-7-oxo-2-phenyl-7H pyrido[1,2,3 de][1,4]benzoxazine-6-carboxylic acid.

Melting point >300° C.

EXAMPLE 17

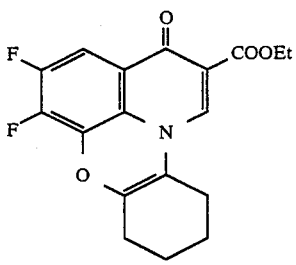

5 g of ethyl 6,7,8-trifluoro-4-hydroxy-3-quinolinecarboxylate, 5 g of 2-chlorocyclohexanone and 6.6 g of $K_2CO_3$ are heated at 90° C. in 40 ml of dimethylformamide for 10 hours. Thereafter, the mixture is concentrated in vacuo. The residue is taken up in water and the mixture is extracted with $CH_2Cl_2$. The organic phase is dried and evaporated. The residue is separated with the aid of a column (silica gel, mobile phase, toluene/ethyl acetate 1:1).

Yield 0.6 g of ethyl 6,7-difluoro-9-oxo-9H-cyclohexa[1,2-b]pyrido-[1',2',3'-de]1,4-benzoxazine-10-carboxylate.

Melting point 198°–208° C.

It will be appreciated that the instant specification and examples are set forth by way of illustration and not limitation, and that various modifications and changes may be made without departing from the spirit and scope of the present invention.

We claim:

1. A 1,8-bridged 4-quinolone-3-carboxylic acid or derivative of the formula

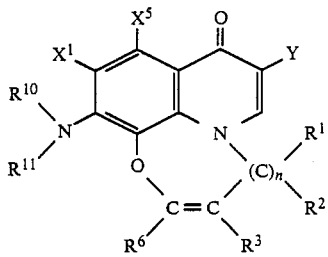

in which
Y represents a carboxyl group, a nitrile group, an ester group —COOR[7] or an acid amide group —CONR[8]R[9],
R[7] represents $C_1$–$C_4$-alkyl, and
R[8] and R[9] independently of one another represent hydrogen or $C_1$–$C_4$-alkyl, and
R[9] can also be phenyl,
X[1] represents hydrogen, nitro, alkyl with 1–3 carbon atoms, or halogen,
X[5] can be hydrogen, halogen or alkyl,
R[10] and R[11], together with the nitrogen atom to which they are bonded, form a 5- or 6-membered heterocyclic ring which can additionally contain the atoms or groups —O—, —S—, —SO—, —SO$_2$—,

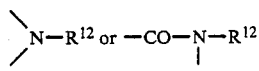

as a ring member and which can optionally be mono-, di- or trisubstituted on the carbon atoms by identical or different substituents from the group consisting of
(a) $C_1$–$C_4$-alkyl, phenyl, cyclohexyl, 2-thienyl, hydroxy, alkoxy with 1 to 3 carbon atoms, amino, methylamino, ethylamino, aminomethyl, methylaminomethyl, ethylaminomethyl, and
(b) phenyl or cyclohexyl each of which is mono-, di- or trisubstituted by chlorine, fluorine, bromine, methyl, phenyl, hydroxy, methoxy, benzyloxy, nitro or piperidino,
R[12] represents hydrogen; a branched or unbranched alkyl, alkenyl or alkinyl group with 1 to 6 carbon atoms, which can optionally be substituted by one or two hydroxyl groups or alkoxy, alkylamino or dialkylamino groups with in each case 1 to 3 carbon atoms per alkyl radical; a cyano group; an alkoxycarbonyl group with 1 to 4 carbon atoms in the alkyl part; a phenylalkyl group which has up to 4 carbon atoms in the alkyl part; a phenacyl radical which is optionally mono- or disubstituted by hydroxyl, methoxy, chlorine or fluorine; an oxoalkyl radical with up to 6 carbon atoms; or furthermore denotes a radical COR[13] or $SO_2R^{14}$,
R[13] represents hydrogen, straight-chain or branched alkyl which has 1 to 4 carbon atoms and is optionally substituted by 1 or 2 substituents from the group consisting of amino, alkoxycarbonyl with 1 to 3 carbon atoms in the alkyl part, carboxyl, alkoxy with 1 to 3 carbon atoms and halogen; alkoxy with 1 to 4 carbon atoms; amino; or alkylamino or dialkylamino with 1 to 5 carbon atoms in the alkyl part, R$^{14}$ represents straight-chain or branched alkyl with 1 to 3 carbon atoms, and R$^1$, R$^2$, R$^3$ and R$^6$ represent hydrogen; an alkyl group with 1-6 carbon atoms which is optionally mono- or polysubstituted by halogen, nitro, cyano, hydroxy, or alkoxy or alkylmercapto with 1-3 carbon atoms in the alkyl part; or represent a phenyl radical, naphthyl radical or 5- or 6-membered heterocyclic radical with N and/or O as heteroatoms each of which is optionally substituted by halogen, nitro, alkyl, alkoxy or alkylmercapto with in each case up to 3 carbon atoms, hydroxyl, phenoxy, phenylthio, naphthoxy, naphthylthio, cyano or an ester radical with 1-3 carbon atoms in the alkyl part, and n denotes 0 or 1, or a pharmaceutically usable hydrate, or an alkali metal, alkaline earch metal, silver or guanidinium salt or an ester thereof.

2. A compound or derivative according to claim 1, in which

X$^5$ can be hydrogen, Cl or F or methyl,

R$^{13}$ represents hydrogen; straight-chain or branched alkyl which has 1 to 4 carbon atoms and is optionally substituted by 1 or 2 substituents from the group consisting of amino, alkoxycarbonyl with 1 to 3 carbon atoms in the alkyl part, carboxyl, alkoxy with 1 to 3 carbon atoms, chlorine, bromine and fluorine; alkoxy with 1 to 4 carbon atoms; amino; or alkylamino or dialkylamino with 1 to 5 carbon atoms in the alkyl part, R$^1$, R$^2$, R$^3$ and R$^6$ represent hydrogen; an alkyl group with 1-6 carbon atoms, which is optionally mono- or polysubstituted by chlorine, fluorine, nitro, cyano, hydroxyl or alkoxy or alkylmercapto with 1-3 carbon atoms in the alkyl part; or a phenyl radical or thiophene, furan, pyrrole, thiazole, pyridine or pyrimidine radical optionally substituted by halogen, nitro, alkyl, alkoxy or alkylmercapto with in each case up to 3 carbon atoms, hydroxyl, phenoxy, phenylthio, naphthoxy, naphthylthio, cyano or an ester radical with 1-3 carbon atoms in the alkyl part.

3. A compound or derivative according to claim 1, in which

R$^7$ is methyl or ethyl,

X$^1$ represents fluorine,

X$^5$ represents hydrogen and

R$^{10}$ and R$^{11}$, together with the nitrogen atom to which they are bonded, form a 5- or 6-membered heterocyclic ring which can additionally contain an oxygen atom or the groups

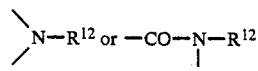

as a ring member and which can optionally be mono- or disubstituted on the carbon atoms by C$_1$-C$_2$-alkyl, cyclohexyl, phenyl which is optionally substituted by chlorine, fluorine, methyl, phenyl, hydroxyl, methoxy, benzyloxy, nitro or piperidino, 2-thienyl or hydroxyl, R$^{12}$ represents hydrogen, a branched or unbranched alkyl group with 1 to 3 carbon atoms which can optionally be substituted by one or two hydroxyl groups, or a phenacyl radical, an oxoalkyl radical with up to 4 carbon atoms or a radical COR$^{13}$, and R$^{13}$ denotes hydrogen or alkyl with one or two carbon atoms.

4. A compound according to claim 1, wherein such compound is 9-fluoro-3-methyl-10-(4-methyl-1-piperazinyl)-7-oxo-7H pyrido[1,2,3 de][1,4]benzoxazine-6-carboxylic acid of the formula

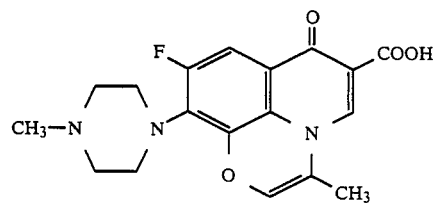

or a pharmaceutically usable hydrate, or an alkali metal, alkaline earth metal, silver or guanidinium slt or an ester thereof.

5. A compound according to claim 1, wherein such compound is 9-fluoro-3-methyl-10-(1-piperazinyl)-7-oxo-7H pyrido[1,2,3 de][1,4]benzoxazine-6-carboxylic acid of the formula

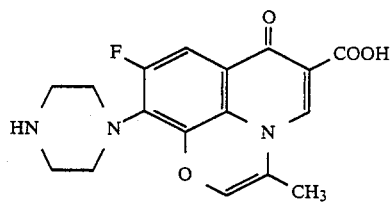

or a pharmaceutically usable hydrate, or an alkali metal, alkaline earth metal, silver or guanidinium salt or an ester thereof.

6. A compound according to claim 1, wherein such compound is 9-fluoro-3-methyl-10-(3-methyl-1-piperazinyl)-7-oxo-7H pyrido[1,2,3 de][1,4]benzoxazine-6-carboxylic acid of the formula

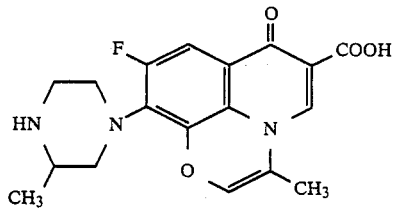

or a pharmaceutically usable hydrate, or an alkali metal, alkaline earth metal, silver or guanidinium salt or an ester thereof.

7. A compound according to claim 1, wherein such compound is 9-fluoro-10-(4-methyl-1-piperazinyl)-7-oxo-7H pyrido[1,2,3 de][1,4]benzoxazine-6-carboxylic acid of the formula

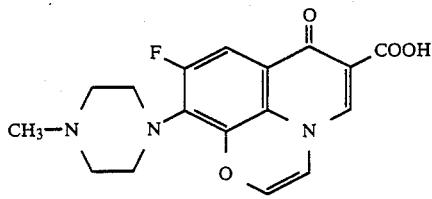

or a pharmaceutically usable hydrate, or an alkali metal, alkaline earth metal, silver or guanidinium salt or an ester thereof.

8. A compound according to claim 1, wherein such compound is 9-fluoro-2-methyl-10-(4-methyl-1-piperazinyl)-7-oxo-7H pyrido[1,2,3 de][1,4]benzoxazine-6-carboxylic acid of the formula

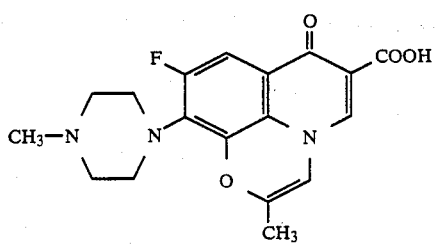

or a pharmaceutically usable hydrate, or an alkali metal, alkaline earth metal, silver or guanidinium salt or an ester thereof.

9. An antibacterial composition comprising an antibacterially effective amount of a compound or addition product according to claim 1 and a diluent.

10. A unit dose of a composition according to claim 9 in the form of a tablet, capsule or ampule.

11. A method of combating bacteria which comprises administering to a patient in need thereof an amount effective therefor of a compound or addition product thereof according to claim 1.

12. The method according to claim 11, wherein such compound is
9-fluoro-3-methyl-10-(4-methyl-1-piperazinyl)-7-oxo-b 7H pyrido[1,2,3 de][1,4]benzoxazine-6-carboxylic acid,
9-fluoro-3-methyl-10-(1-piperazinyl)-7-oxo-7H pyrido[1,2,3 de][1,4]benzoxazine-6-carboxylic acid,
9-fluoro-3-methyl-10-(3-methyl-1-piperazinyl)-7-oxo-7H pyrido[1,2,3 de][1,4]benzoxazine-6-carboxylic acid,
9-fluoro-10-(4-methyl-1-piperazinyl)-7-oxo-7H pyrido[1,2,3 de][1,4]benzoxazine-6-carboxylic acid, or
9-fluoro-2-methyl-10-(4-methyl-1-piperazinyl)-7-oxo-7H pyrido[1,2,3 de][1,4]benzoxazine-6-carboxylic acid,
or a pharmaceutically usable hydrate, or an alkali metal, alkaline earth metal, silver or guanidinium salt or an ester thereof.

* * * * *